United States Patent [19]

Thiele et al.

[11] 4,115,393
[45] Sep. 19, 1978

[54] PYRIDYL ALKYL ESTERS OF SUBSTITUTED PHENOXY ALKANOIC ACIDS HAVING THE ABILITY TO REDUCE THE LEVEL OF FATTY SUBSTANCES IN THE BLOOD

[75] Inventors: Kurt Thiele, Zofingen; Quazi Ahmed, Strengelbach; Rudolf Adrian, Vordemwald; Ulrich Jahn, Zofingen, all of Switzerland

[73] Assignee: Siegfried Aktiengesellschaft, Zofingen, Switzerland

[21] Appl. No.: 773,145

[22] Filed: Mar. 1, 1977

Related U.S. Application Data

[63] Continuation-in-part of Ser. No. 536,120, Dec. 24, 1974, abandoned.

[30] Foreign Application Priority Data

Mar. 28, 1974 [CH] Switzerland .......................... 4355/74
Nov. 18, 1974 [CH] Switzerland ........................ 15329/74

[51] Int. Cl.² .............................................. C07D 213/55
[52] U.S. Cl. ...................... 260/295.5 R; 260/294.8 G; 424/263
[58] Field of Search ................... 260/295.5 R, 294.8 G

[56] References Cited

U.S. PATENT DOCUMENTS 3,622,587 11/1971 Carlson et al. ................ 260/295.5 R

OTHER PUBLICATIONS

Burger, Medicinal Chemistry, Second Edition, p. 497, Interscience Pub., 1960.
Culvenor, Reviews Pure and Applied Chemistry, vol. 3, (1953).

*Primary Examiner*—Alan L. Rotman
*Attorney, Agent, or Firm*—Finnegan, Henderson, Farabow & Garrett

[57] ABSTRACT

Compounds of the formula

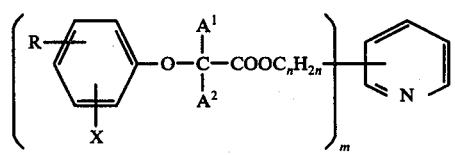

wherein R represents hydrogen, halogen, hydroxy or alkyl or alkoxy containing from 1 to 4 carbon atoms;
X represents benzyl, benzyloxy or benzylthio, or benzyl, benzyloxy or benzylthio substituted by a said radical R;
$A^1$ and $A^2$ which can be the same or different are hydrogen or alkyl radical containing up to 10 carbon atoms such that the total number of carbon atoms in $A^1$ and $A^2$ is not more than 10;
$n$ is an integer of from 1 to 3;
$m$ is 1 or 2;
and pharmacologically acceptable salts thereof.

These compounds have pharmaceutical utility by virtue of their ability to reduce the level of fatty substances in the blood.

8 Claims, No Drawings

PYRIDYL ALKYL ESTERS OF SUBSTITUTED PHENOXY ALKANOIC ACIDS HAVING THE ABILITY TO REDUCE THE LEVEL OF FATTY SUBSTANCES IN THE BLOOD

This application is a continuation-in-part of our copending Application Ser. No. 536,120 filed Dec. 24th, 1974, now abandoned.

This invention relates to novel benzylphenoxyalkanoic acids and esters and salts thereof, to methods for the preparation thereof, to pharmaceutical compositions comprising the same and to use of the compounds in reducing cholesterol and triglyceride levels in blood.

Aryloxy carboxylic acid esters have been proposed for use in the therapy of excessive cholesterol and triglyceride levels in the blood in British Patent specification No. 860,303. One of the substances described in British Patent specification No. 860,303, namely the methyl ester of 2-(4'-chlorophenoxy)-isobutyric acid having the short name "Clofibrat" as recommended by World Health Organisation, has so far acquired considerable importance in the clinical treatment of human beings. It has since been found that many new compounds of related structure are superior to Clofibrat in their cholesterol-reducing effect to a surprisingly high extent. Phenoxy-alkanoic acids and esters thereof of such type are described, for example, in U.S. Pat. Nos. 3,546,273 filed 1st June, 1967 and 3,948,973 which is a continuation-in-part of Ser. No. 284,577 filed Aug. 19th, 1972.

It has now been found that compounds having hypocholesterolaemic and hypolipaemic activities substantially greater than compounds mentioned in any of the aforesaid publications possess the general formula

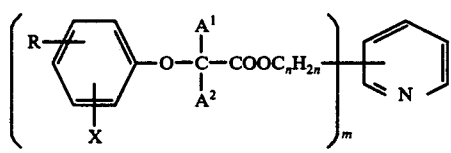

wherein R represents hydrogen, halogen, hydroxy or alkyl or alkoxy containing from 1 to 4 carbon atoms;

X represents benzyl, benzyloxy or benzylthio, or benzyl, benzyloxy or benzylthio substituted by a said radical R;

$A^1$ and $A^2$ which can be the same or different are hydrogen or alkyl radicals containing up to 10 carbon atoms such that the total number of carbon atoms in $A^1$ and $A^2$ is not more than 10;

$n$ is an integer of from 1 to 3, and $m$ is 1 or 2, and pharmacologically acceptable salts thereof.

This invention also provides a process for the production of a compound according to the present invention, wherein a phenol of the general formula

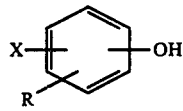

wherein X and R have the meanings set out hereinabove, or a corresponding alkali metal or alkaline earth metal phenolate is reacted with a compound of the general formula

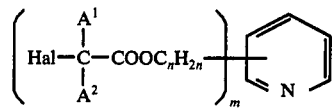

in which Hal is a halogen atom, and $A^1$, $A^2$, $n$ and $m$ have the meanings set out hereinabove, and recovering the said compound either as such or as pharmacologically acceptable acid addition salts thereof.

In an alternative method for the production of compounds according to the present invention a phenol of the general formula

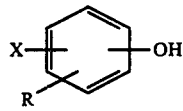

wherein X and R have the aforesaid meanings or a corresponding alkali metal or alkali earth metal phenolate is reacted in the presence of an at least trihalogenated methane derivative and in the presence of a strong base with a ketone of formula $A^1$-CO-$A^2$ in which $A^1$ and $A^2$ have the meanings set out hereinabove, and (a) if necessary esterifying, either as such or as a reactive derivative thereof such as an acid chloride or an acid anhydride, a carboxyl group in the reaction product so obtained or obtained by alkaline hydrolysis of a reaction product so obtained, with a hydroxy terminated compound of the general formula

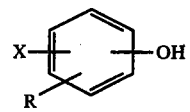

or (b) when the reaction product of the compound of general formula II, the trihalogenated methane derivative and the ketone contains an alkoxy carbonyl group, subjecting the reaction product to a ester exchange with an ester of general formula IV.

As previously indicated, with compounds according to the invention, R can be, inter alia, halogen atoms. They may be fluorine, chlorine, bromine or iodine, but particularly when substituting a benzyl, benzyloxy or benzylthio group is preferably chlorine, more particularly chlorine in the p'- position. R may also be alkyl containing from 1 to 4 carbon atoms, especially when substituting the phenoxy group. R, particularly when substituting the phenoxy group, may be alkyl containing from 1 to 4 carbon atoms, more particularly methyl, ethyl, n-propyl or isopropyl, or n-butyl isobutyl or t-butyl, or alkoxy containing from 1 to 4 carbon atoms for example, methoxy, ethoxy, propoxy(n- or iso-) or butoxy (n-, iso- or tert.-). When substituting the phenoxy group, a radical R or other than hydrogen may be in the ortho or meta position with regard to the linkage between the two benzene rings. Preferred compounds according to the present invention are those containing a p-benzylphenoxy group, in which the benzyl group is preferably substituted in the p'- position by chlorine.

The esterifying group in the compounds according to the present invention may be pyridyl-substituted methyl, ethyl, n-propyl or isopropyl. The pyridyl group is preferably substituted by the remainder of the molecule in the 3- position particularly when it is only mono-substituted. When it is di- substituted it is preferably substituted in the 2- and 6- positions. Mono- substitution in the 3- and 4- positions and di- substitution in the 2,3-, 2,4- and 3,4- positions of the pyridine ring is also possible.

It is preferred that with compounds of this invention, the carbon atom lying between the ether oxygen atom and the carboxyl group be asymetric. Moreover it is preferred that both $A^1$ and $A^2$ are alkyl in which preferred case it is required that the two alkyl groups differ in their carbon atom content and contain at least one carbon atom such that the total carbon atom content of the two alkyl groups is not more than 10. Such alkyl groups can thus be methyl, ethyl, n-propyl or iso-propyl, n-butyl, isobutyl or t-butyl or any of the pentyl, hexyl, heptyl, octyl or nonyl groups. The nature of the optical isomerism based on the carbon atom linking the ether oxygen atom and the carboxyl group is not critical. Both D- and L- forms of the compound as well as racemates thereof possess hypocholesterolaemic and hypolipaemic activity.

The compounds of this invention may either be in free base form or in the form of pharmacologically acceptable acid addition and quaternary ammonium salts thereof. Such salts may be formed using a variety of organic and inorganic acids, such as sulphuric, phosphoric, hydrochloric, hydrobromic, hydroiodic, sulphamic, citric, lactic, oleic succinic, tartaric, cinnamic, acetic, benzoic, gluconic, ascorbic and related acids. Similarly the quaternary ammonium salts may be derived from a variety of organic esters of sulphuric, hydrohalic and aromatic sulphonic acids. The ones suggested are methyl chloride and bromide, ethyl chloride, propyl chloride, butyl chloride, isobutyl chloride, benzyl chloride and bromide, phenethyl bromide, naphthyl methyl chloride, dimethyl sulphate, methyl benzene sulphonate, ethyl toluene sulphonate, ethylene chlorohydrin, propylene chlorohydrin, methallyl bromide and crotyl bromide.

As will be appreciated from the foregoing, two basic preparative methods have been found to be particularly satisfactory for use in the production of compounds according to the present invention.

In the first such method, a phenol is trated with a compound of general formula III hereinabove. The halogen atom in the compound of general formula III is preferably chlorine or bromine. Thus, for example, the compound 4-(4'-chlorobenzyl)-phenol can be condensed with the ethyl ester of 2-bromo-2-methyl butyric acid and the condensation product thereby obtained can be subjected to hydrolytic cleavage of the ethyl group to form 2-[4-(4'-chlorobenzyl)-phenoxy]-2-methylbutyric acid. This acid can be reacted with thionyl chloride to form its acid chloride which can be esterified by reaction with a hydroxy alkylene substituted pyridine.

Although a multistage preparative process for a compound according to the present invention has been described in the preceding paragraph, it is possible to use in place of an ethyl ester as indicated in the specific example, a pyridyl-substituted alcohol of the aforesaid general formula IV.

In the second aforesaid process for the production of compounds according to the present invention, a phenol of general formula II is reacted with a ketone of formula $A^1$-CO-$A^2$ in the presence of an at least trihalogenated methane derivative. When the trihalogenated methane derivative is a simple halomethane, for example chloroform or carbon tetrachloride, the reaction product will possess the general formula

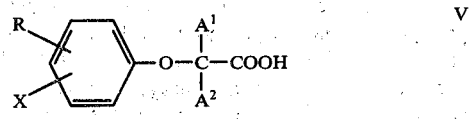 V

This compound can be esterified as aforesaid with the compound of general formula IV.

In an alternative reaction sequence applicable in the case when the trihalogenated methane derivative reacted with the phenol in the presence of the ketone and a strong base which can be sodium or potassium hydroxide contains a fourth substituent which is not a halogen atom and the product contains an alkoxy carbonyl group, the reaction product can be subjected then to ester exchange with a suitable pyridyl-substituted alcohol to produce a compound according to this invention.

Compounds of the general formula I have been found to be particularly effective agents for lowering the cholesterol level of blood. Although as mentioned above, aryloxy carboxylic esters have been proposed for use in the therapy of excessive cholesterol and triglyceride levels in the blood in British Patent specification No. 860,303, in particular the compound Clofibrat the compounds of this invention are generally more effective.

Results of tests carried out on animals are set out in the following table, these results having been obtained with a representative selection of compounds according to this invention in comparison with Clofibrat (comparative product A) and a simple ester of a benzyl phenoxy alkanoic acid, 2-[4-(4'-chlorobenzyl)-phenoxy]-2-methylpropionic acid ethyl ester (comparative product B). In the table which follows, the various columns are given reference numerals having the following meanings (1) Sets out the identification of the test substance in question;

(2) Indicates the nature of the group etherifying the hydroxy alkanoic acid pyridyl-alkyl ester;

(3) & (4) Denote the alkyl groups $A^1$ and $A^2$;

(5) Denotes the esterifying moiety;

(6) Denotes the quantities of the test substance in mg/kg of body weight of the animal — rat (a) or mouse (b) which were orally adminstered to the test animals in tests to determine the acute toxicity (LD50) therefor;

(7) Shows the quantities of the test substance in mg/kg of body weight of rats undergoing tests which were orally adminstered thereto to determine the daily dose which lowers the serum cholesterol level by 25% (ED25). Indicated in columns (8) and (9) are the therapeutic index values calculated from the numerical values of the preceding columns, that is to say the $LD50_{rat}/ED25_{rat}$ and $LD50_{mouse}/ED25_{rat}$ ratios, respectively;

(8) & (9) Are the therapeutic index values calculated from the numerical values of the preceding columns, that is to say the $LD50_{rat}/ED25_{rat}$ and $LD50_{mouse}/ED25_{rat}$ ratios respectively.

In column 2, the meanings of the symbols employed are as follows:

α = p-benzylphenyl
β = p-(p'-chlorobenzyl)-phenyl

To determine the LD50 values, tests were carried out using male animals. After a single administration of the test substances, the animals were observed, their body weight being monitored, for at least seven days until toxic symptoms had faded. The volume of substances injected amounted to 10 ml/kg.

To determine the $ED_{25}$ values out in the Table, male rats weighing 100–200 g were given the test substance once daily orally, emulsified in 3% gum arabic in a volume of 1 ml/100 g of body weight. Administration was usually commenced on Monday and continued up to and including Thursday of a second week. The final treatment on the Thursday was given at about 16.00 hours. Then the rats, which throughout the experiment had been kept in dosage groups of 8–10 in size 3 Makrolon cages, were kept fasting. On the Friday morning, the animals were sacrificed by carotid section under ether narcosis. After centrifugation of the blood obtained in this way, the total cholesterol content of the serum was determined on a Beckman or DBG spectrophotometer by the method of Richterich, R. (Clinical Chemistry, S. Karger,/New York 1965, p. 232). The average group values of the Table were compared with those from a simultaneously investigated control group.

25% per oral administration, whereas only 13 mg/kg of compound No. 26074 were required to achieve the same effect.

It will be appreciated that for therapeutic use, the compounds of the invention can be made up, in accordance with well known pharmaceutical techniques, into compositions having as an essential active ingredient a compound of the invention in association with a pharmaceutical carrier therefor. If desired, the compositions can be made up in a dosage unit form suitable for the particular mode of administration, the quantity of active ingredient in each dosage unit being such that one or more units are required for each therapeutic administration. The dosage unit may exist, for example, in the form of a tablet, sugar coated pill, capsule or packaged powder for oral administration, or in the form of a sterile injectable solution or suspension, if desired contained in an ampoule, for parenteral administration. The dosage unit preferably contains from 5 to 300 milligrams of active substance. The compounds of the present invention may also be incorporated in emulsions or solutions for oral administration. For a person of average build, it is expected that a dosage of from 0.02 to 1.5 gram per day would be suitable for therapeutic purposes.

The following examples illustrate the invention. Altough detailed examples only describe the preparation of a small number of compounds according to the present invention, further compounds have been prepared whose properties are summarised at the end of the examples.

TABLE

| (1) | (2) | (3) | (4) | (5) | (6)(a) | (6)(b) | (7) | (8) | (9) |
|---|---|---|---|---|---|---|---|---|---|
| Comparative Product A | | | | | — | 2350 | 160 | — | 15 |
| Comparative Product B | | | | | — | 3000 | 54 | — | 120 |
| 16576 | α | CH₃ | CH₂CH₂CH₃ | —CH₂—(pyridyl) | — | 11000 | 13 | — | 846 |
| 31475 | β | CH₃ | CH₂CH₂CH₃ | —CH₂—(pyridyl)·HCl | 5600 | 5300 | 6.5 | 862 | 815 |
| 16375 | β | CH₃ | CH₂CH₂CH₃ | —CH₂—(pyridyl) | 10000 | 5600 | 4 | 2500 | 1400 |
| 33374 | β | CH₃ | C₂H₅ | —CH₂—(pyridyl)·HCl | 7350 | 5900 | 11.9 | 618 | 496 |
| 26074 | β | CH₃ | CH₃ | —CH₂—(pyridyl)·HCl | — | 3000 | 14 | — | >214 |
|  | β | H | H | —CH₂—(pyridyl) | 2700 | — | 28 | — | 96 |

In addition to possessing the strong hypocholesterolaemic effect which can be seen from the table, the compounds of the present invention also lower considerably the triglyceride content of the blood and are in this respect again many times better than Clofibrat. By way of example, hypotriglyceridaemia produced in rats by adding fructose to their drinking water was lowered by Clofibrat administered in a dosage of 85 mg/kg by

EXAMPLE 1

4-(4'-chlorobenzyl)-phenoxyacetic acid (3-pyridyl)-methyl ester

A solution of 6.0 g (0.02 mol) of p-(p'-chlorobenzyl)-phenoxy acetyl chloride in 50 ml of anhydrous benzene was added to a solution of 2.18 g (0.02 mol) of 3-hydroxymethyl pyridine in 20 ml of anhydrous pyridine. The mixture was stirred for 45 minutes at room temperature and thereafter heated for 6.5 hours at reflux temperature. The solvent was then evaporated in a Buchi rotary evaporator under reduced pressure; the residue was taken up in 10% aqueous KHCO₃ solution and extracted with dichloromethame. The organic phase was washed with water and dried over anhydrous magnesium sulphate. A residue was obtained, from which 4.0 g of product in the form of white lustrous needles and a melting point of 77°-78° C. could be recovered by crystallisation from ether/petroleum ether.

| $C_{21}H_{18}ClNO_3$ | | (367.5) | | | |
|---|---|---|---|---|---|
| Calculated: | C 68.57 | H 4.90 | N 3.81 | Cl | 9.66 |
| Found: | C 68.31 | H 4.52 | N 3.41 | Cl | 10.24 |

EXAMPLE 2

Bis- 4-(4'-chlorobenzyl)-phenoxyacetic acid (2,6-pyridyl) dimethyl ester

A solution of 6.0 g (0.02 mol) of p-(p'-chlorobenzyl)-phenoxy-acetyl chloride in 50 ml of anhydrous toluene was added to a solution of 1.39 g (0.01 mol) of 2,6-bis-(hydroxymethyl)-pyridine in 15 ml of anhydrous pyridine. After boiling for 24 hours under reflux and working up in a similar manner to that used in the preceding Example, a residue was obtained which yielded 4.0 g of product in the form of lustrous white crystals of melting point 78° C. after recrystallisation from dichloromethane/ether/petroleum ether.

| $C_{37}H_{31}Cl_2NO_6$ | | (656.5) | | | |
|---|---|---|---|---|---|
| Calculated: | C 67.68 | H 4.76 | N 2.13 | Cl | 10.80 |
| Found: | C 67.67 | H 4.84 | N 1.77 | Cl | 11.14 |

EXAMPLE 3

2-Methyl-2- 4-(4'-chlorobenzyl)-phenoxy -butyric acid-(3-oxymethylpyridine)-ester hydrochloride

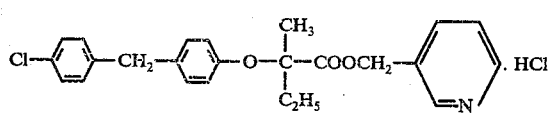

78 g (0.232 mol) of 2-methyl-2- 4-(4'-chlorobenzyl)-phenoxy -butyryl chloride are dissolved in 300 ml of anhydrous benzene and 200 ml of anhydrous pyridine and then a solution of 27 g (0.247 mol) of 3-hydroxymethyl pyridine in 20 ml of anhydrous benzene is added. The mixture is heated for 5 hours and while stirring at reflux temperature and is thereafter concentrated by evaporation in Buchi rotary evaporator. The brown residue is taken up in ether, the solution is extracted with water, dried over MgSO₄ and again evaporated under reduced pressure. The residue is dissolved in cyclohexane is dissolved in ether and treated with a solution of hydrogen chloride in ether. The crystalline precipitate, after being recrystallised from dichloromethane/ether, yields 40.0 g of hydrochloride as white lustrous crystals of melting point 111°-114° C.

| $C_{24}H_{24}ClNO_3$ | HCl | (446.3) | | | |
|---|---|---|---|---|---|
| Calculated: | | C 64.58 | H 5.65 | N 3.14 | O 10.75 Cl 15.89 |
| Found: | | C 64.95 | H 5.65 | N 2.98 | O 10.46 Cl 16.00 |

The 2-methyl-2-[4-chlorobenzyl]-phenoxy -butyryl chloride used as starting substance can be obtained from the corresponding ethyl ester which is saponified with alcoholic caustic potash solution to yield the free acid which is then converted with thionyl chloride into the acid chloride. The aforesaid ethyl ester may be obtained by the following procedure:

87.0 g (0.4 mol) of 4-chloro-4'-hydroxydiphenylmethane are heated together with 27.0 g (0.2 mol) of anhydrous potassium carbonate in 350 ml of anhydrous xylene for 30 minutes to reflux temperature, whereafter a solution of 83.5 g (0.4 mol) of 2-bromo-2-ethyl-2-methyl acetic acid ethyl ester in 50 ml of anhydrous xylene is added. The mixture is kept for 24 hours and with vigorous stirring at reflux temperature. After filtering off the precipitated potassium bromide and evaporating the solvent in a Buchi rotary evaporator, the residue is taken up in ether and extracted with normal sodium hydroxide solution. The ether extracts are washed with water, dried over MgSO₄ and concentrated by evaporation. The brown oil (82.0 g) thereby obtained is dissolved in n-hexane and filtered through a column of 200 g of basic Al₂O₃. After evaporating the solvent and distillation at reduced pressure, 34.7 g of pure product are obtained with the boiling point 200°-204° C./0.01-0.1 mm Hg.

| $C_{20}H_{23}ClO_3$ | (346.8) | | | |
|---|---|---|---|---|
| Calculated: | C 69.25 | H 6.68 | O 13.84 | Cl 10.22 |
| Found: | C 69.16 | H 6.66 | O 13.84 | Cl 10.27 |

EXAMPLE 4

2-Methyl-2-[4-(4'-chlorobenzyl)-phenoxy]-valeric acid-3-pyridylmethyl -ester hydrochloride

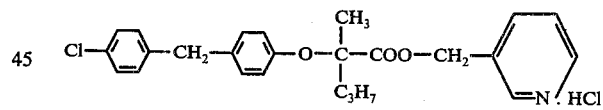

262 g. (0.75 ml) of 2-methyl-2-[4-(4'-chlorobenzyl)-phenoxy]-valeroyl chloride are dissolved in 900 ml of anhydrous benzene and 250 ml of anhydrous pyridine and then a solution of 87 g. (0.80 ml) of 3-hydroxymethyl pyridine in 200 ml anhydrous benzene is added. The mixture is heated under reflux for one hour and is thereafter concentrated by evaporation in a Buchi rotary evaporator. The brown residue is stirred with saturated sodium becarbonate solution, extracted with methylene dichloride in water. The organic phase is dried with magnesium sulphate and again evaporated under reduced pressure. The residue is dissolved in cyclohexane and filtered through a column of 900 g. of basic Al₂O₃. The light brown oil obtained by distilling off the cyclohexane is dissolved in ether and treated with a solution of hydrogen chloride in ether. The crystalline deposit yields, after recrystallisation from methylene dichloride/ether, 190 g. of hydrochloride as white crystals melting at 112°-114° C. Elemental analysis of this product gave the following result:

| $C_{24}H_{27}ClNO_3 \cdot HCl$ | | | | | |
|---|---|---|---|---|---|
| Calculated: | C 65.22 | H 5.91 | N 3.04 | O 10.43 | Cl 15.40 |
| Found: | C 65.21 | H 5.94 | N 2.69 | O 10.41 | Cl 15.74 |

The 2-methyl-2-[4-(4'-chlorobenzyl)-phenoxy]-valeroyl chloride used as starting material can be obtained in a procedure in which the corresponding ethyl ester is hydrolysed with alcoholic potassium hydroxide solution, the corresponding free acid obtained then being reacted with thionyl chloride.

Other compounds according to the present invention which have been produced by the procedure of Examples 1 to 4 have been the following:

I—2-methyl-2-[4-benzylphenoxy]valeric acid-(3-pyridyl methyl)-ester (Example 1 procedure)

II—2-methyl-2-[4-(4'-chlorobenzyl)phenoxy]valeric acid-(3-pyridylmethyl)-ester (Example 1 procedure)

III—2-methyl-2-[4-(4'-chlorobenzyl)-phenoxy]-propionic acid-(3-pyridylmethyl)-ester hydrochloride (Example 3 or 4 procedure).

We claim:
1. A compound of the general formula

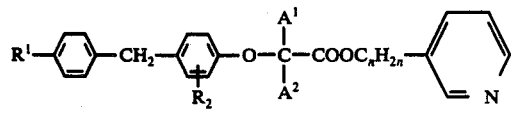

wherein $R^1$ and $R^2$ are hydrogen, halogen, hydroxy or alkyl or alkoxy containing from 1 to 4 carbon atoms;

$A^1$ and $A^2$ which can be the same or different are hydrogen or alkyl radical containing up to 10 carbon atoms such that the total number of carbon atoms in $A^1$ and $A^2$ is not more than 10; and $n$ is an integer of from 1 to 3, and pharmacologically acceptable salts thereof.

2. A compound according to claim 1, wherein $A^1$ and $A^2$ are different alkyl groups containing from 1 to 9 carbon atoms such that the total number of carbon atoms possessed by $A^1$ and $A^2$ is not greater than 10.

3. A compound as claimed in claim 2, wherein $R^1$ is chlorine and $R^2$ is hydrogen.

4. A compound according to claim 1, wherein $n$ is 1.

5. A compound according to claim 1 which is 2-methyl-2-[4-benzylphenoxy]valeric acid-(3-pyridyl methyl)-ester and pharmacologically acceptable salts thereof.

6. A compound according to claim 1 which is 2-methyl-2-[4-(4'-chlorobenzyl)phenoxy]valeric acid-(3-pyridylmethyl)-ester, and pharmacologically acceptable salts thereof.

7. A compound according to claim 1 which is 2-methyl-2-[4-(4'-chlorobenzyl)-phenoxy]-butyric acid-(3-oxymethylpyridine)-ester, and pharmacologically acceptable salts thereof.

8. A compound according to claim 1 which is 2-methyl-2-[4-(4'-chlorobenzyl)-phenoxy]-propionic acid-(3-pyridylmethyl)-ester, and pharmacologically acceptable salts thereof.